(12) United States Patent
Chiu

(10) Patent No.: US 11,279,618 B2
(45) Date of Patent: Mar. 22, 2022

(54) OZONE WATER SUPPLY APPARATUS AND OZONE GENERATION DEVICE

(71) Applicant: CASHIDO CORPORATION, Miaoli County (TW)

(72) Inventor: Chun-Lung Chiu, Miaoli County (TW)

(73) Assignee: CASHIDO CORPORATION, Miaoli County (TW)

( * ) Notice: Subject to any disclaimer, the term of this patent is extended or adjusted under 35 U.S.C. 154(b) by 169 days.

(21) Appl. No.: 16/809,550

(22) Filed: Mar. 5, 2020

(65) Prior Publication Data
US 2021/0276867 A1   Sep. 9, 2021

(51) Int. Cl.
*C01B 13/11* (2006.01)
*A61L 2/18* (2006.01)
(Continued)

(52) U.S. Cl.
CPC .......... *C01B 13/115* (2013.01); *A61L 2/183* (2013.01); *A61L 2/26* (2013.01); *C02F 1/78* (2013.01); *E03C 1/0404* (2013.01); *A61L 2202/11* (2013.01); *C01B 2201/62* (2013.01); *C02F 2201/782* (2013.01); *C02F 2303/02* (2013.01); *C02F 2303/04* (2013.01); *C02F 2307/06* (2013.01)

(58) Field of Classification Search
CPC ....... C01B 13/115; C01B 13/10; C01B 13/11; C01B 2201/00–90; A61L 2/183; A61L 2/26; A61L 2202/11; C02F 1/78; C02F 2201/782; C02F 2303/02; C02F 2303/04; C02F 2307/06; C02F 1/441; C02F 1/003; C02F 2209/42; C02F 1/008; C02F 2101/12; E03C 1/0404; E03C 1/046; E03C 1/055; E03C 2201/40; B01J 19/08; B01J 19/088; Y10T 137/9464; B01D 61/12; B01D 61/08; C25B 15/08; C25B 1/13; C25B 9/08; C25B 9/10; C25B 11/03; C25B 15/02
See application file for complete search history.

(56) References Cited

U.S. PATENT DOCUMENTS

2006/0266683 A1\* 11/2006 Sung .................. E03C 1/08
                                                                210/198.1
2011/0085934 A1\* 4/2011 Joshi .................. A61L 2/24
                                                                422/5

(Continued)

*Primary Examiner* — Xiuyu Tai
(74) *Attorney, Agent, or Firm* — Li & Cai Intellectual Property Office

(57) ABSTRACT

An ozone water supply apparatus and an ozone supply device are provided. The ozone generation device includes a Venturi tube and an ozone generation module connected to the Venturi tube. The ozone generation module includes a circuit unit, an ozone-activated tube, and a launcher, the latter two of which are electrically coupled to the circuit unit. The launcher includes a transparent tube, a floating body arranged in the transparent tube, and an optical detector arranged outside of the transparent tube and electrically coupled to the circuit unit. When a gas flows through the transparent tube so as to move the floating body along the transparent tube, the optical detector is configured to detect the movement of the floating body, so that the ozone-activated tube can be driven by the circuit unit to excite the gas to become an ozone that floats toward the Venturi tube.

10 Claims, 8 Drawing Sheets

(51) Int. Cl.
  *A61L 2/26*   (2006.01)
  *E03C 1/04*   (2006.01)
  *C02F 1/78*   (2006.01)

(56) References Cited

U.S. PATENT DOCUMENTS

| | | | |
|---|---|---|---|
| 2012/0039751 A1* | 2/2012 | Shenberg | A61L 2/183 422/119 |
| 2012/0266983 A1* | 10/2012 | Tsai | E03C 1/046 137/801 |
| 2013/0206604 A1* | 8/2013 | Lutz | C01B 13/11 205/337 |
| 2014/0154141 A1* | 6/2014 | Russell | A23L 3/003 422/119 |
| 2018/0141844 A1* | 5/2018 | Macey | C02F 1/008 |
| 2019/0001006 A1* | 1/2019 | Rodenbeck | A61L 2/18 |
| 2021/0187142 A1* | 6/2021 | Cajauskis | A61L 2/24 |

* cited by examiner

US 11,279,618 B2

OZONE WATER SUPPLY APPARATUS AND OZONE GENERATION DEVICE

FIELD OF THE DISCLOSURE

The present disclosure relates to a fluid supply apparatus, and more particularly to an ozone water supply apparatus and an ozone generation device.

BACKGROUND OF THE DISCLOSURE

Ozone water has sterilizing and deodorizing effects, so that the ozone water is widely used in various fields (e.g., as a tableware disinfectant or a medical device disinfectant). Conventional ozone generation devices use the operation principle of a Venturi tube to mix ozone and water with each other. However, how ozone can be instantaneously mixed with water when supplying water has become an important subject in this field.

SUMMARY OF THE DISCLOSURE

In response to the above-referenced technical inadequacies, the present disclosure provides an ozone water supply apparatus and an ozone generation device to effectively improve the issues associated with conventional ozone generation devices.

In one aspect, the present disclosure provides an ozone water supply apparatus, which includes a faucet device and an ozone generation device. The ozone generation device includes a Venturi tube and an ozone generation module. The Venturi tube includes a first entrance connected to the faucet device, a second entrance, and an exit. When water flows from the faucet device to the Venturi tube through the first entrance and flows out of the Venturi tube through the exit, the Venturi tube is configured to form a negative pressure at the second entrance. The ozone generation module includes a circuit unit, at least one ozone-activated tube, and a launcher. The at least one ozone-activated tube is electrically coupled to the circuit unit and is in spatial communication with the Venturi tube through the second entrance. The launcher is electrically coupled to the circuit unit, and includes a top retainer, a bottom retainer, a first transparent tube, a floating body, at least one first optical detector, a second transparent tube, a horizontal member, and a second optical detector. The bottom retainer is spaced apart from the top retainer along a vertical direction. The top retainer has an air-flow exit in spatial communication with the at least one ozone-activated tube, and the bottom retainer has an air-flow entrance. The first transparent tube has two opposite ends respectively fixed to the top retainer and the bottom retainer and being respectively in spatial communication with the air-flow exit and the air-flow entrance. The floating body is arranged in the first transparent tube. When a gas flows through the first transparent tube by passing through the air-flow entrance and the air-flow exit, the gas drives the floating body to move from the bottom retainer toward the top retainer. The at least one first optical detector is electrically coupled to the circuit unit and is arranged outside of the first transparent tube for detecting a movement of the floating body. The second transparent tube has two ends respectively fixed to the top retainer and the bottom retainer. The second transparent tube has a space therein. The horizontal member is arranged in the second transparent tube. When the ozone generation module is at a slanting position by an external force, the horizontal member is moved along the second transparent tube. The second optical detector is electrically coupled to the circuit unit and is arranged outside of the second transparent tube for detecting a movement of the horizontal member. When the second optical detector obtains that the ozone generation module is at the slanting position by detecting the movement of the horizontal member, the second optical detector stops the operation of the ozone generation module through the circuit unit. When the Venturi tube forms the negative pressure at the second entrance, the gas flows into the at least one ozone-activated tube by passing through the air-flow entrance, the first transparent tube, and the air-flow exit so as to drive the floating body to move from the bottom retainer toward the top retainer. When the movement of the floating body is detected by the at least one first optical detector, the at least one first optical detector drives the at least one ozone-activated tube through the circuit unit, so that at least one ozone-activated tube excites the gas to become an ozone that flows toward the second entrance.

In one aspect, the present disclosure provides an ozone generation device, which includes a Venturi tube and an ozone generation module. The Venturi tube includes a first entrance, a second entrance, and an exit. The Venturi tube is configured to provide a water to flow there-into through the first entrance and to flow there-out through the exit so as to form a negative pressure at the second entrance. The ozone generation module includes a circuit unit, at least one ozone-activated tube, and a launcher. The at least one ozone-activated tube is electrically coupled to the circuit unit and is in spatial communication with the Venturi tube through the second entrance. The launcher is electrically coupled to the circuit unit, and includes a top retainer, a bottom retainer, a first transparent tube, a floating body, at least one first optical detector, a second transparent tube, a horizontal member, and a second optical detector. The bottom retainer is spaced apart from the top retainer along a vertical direction. The top retainer has an air-flow exit in spatial communication with the at least one ozone-activated tube, and the bottom retainer has an air-flow entrance. The first transparent tube has two opposite ends respectively fixed to the top retainer and the bottom retainer and being respectively in spatial communication with the air-flow exit and the air-flow entrance. The floating body is arranged in the first transparent tube. When a gas flows through the first transparent tube by passing through the air-flow entrance and the air-flow exit, the gas drives the floating body to move from the bottom retainer toward the top retainer. The at least one first optical detector is electrically coupled to the circuit unit and is arranged outside of the first transparent tube for detecting a movement of the floating body. The second transparent tube has two ends respectively fixed to the top retainer and the bottom retainer. The second transparent tube has a space therein. The horizontal member is arranged in the second transparent tube. When the ozone generation module is at a slanting position by an external force, the horizontal member is moved along the second transparent tube. The second optical detector is electrically coupled to the circuit unit and is arranged outside of the second transparent tube for detecting a movement of the horizontal member. When the second optical detector obtains that the ozone generation module is at the slanting position by detecting the movement of the horizontal member, the second optical detector stops the operation of the ozone generation module through the circuit unit. When the Venturi tube forms the negative pressure at the second entrance, the gas flows into the at least one ozone-activated tube by passing through the air-flow entrance, the first transparent tube, and the air-flow exit so as to drive the floating body to move from the bottom retainer toward the top retainer. When the movement of the floating body is detected by the at least one first optical detector, the at least one first optical detector drives the at least one ozone-activated tube through the circuit unit, so that at least one ozone-activated tube excites the gas to become an ozone that flows toward the second entrance.

Therefore, the ozone water supply apparatus or the ozone generation device of the present disclosure can use the negative pressure generated by the structure of the Venturi tube to drive the gas to blow against and move the floating body, so that the first optical detector can detect the movement of the floating body to instantly obtain a time point at which an ozone needs to be generated. Accordingly, the ozone-activated tube can instantly generate ozone toward the Venturi tube.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
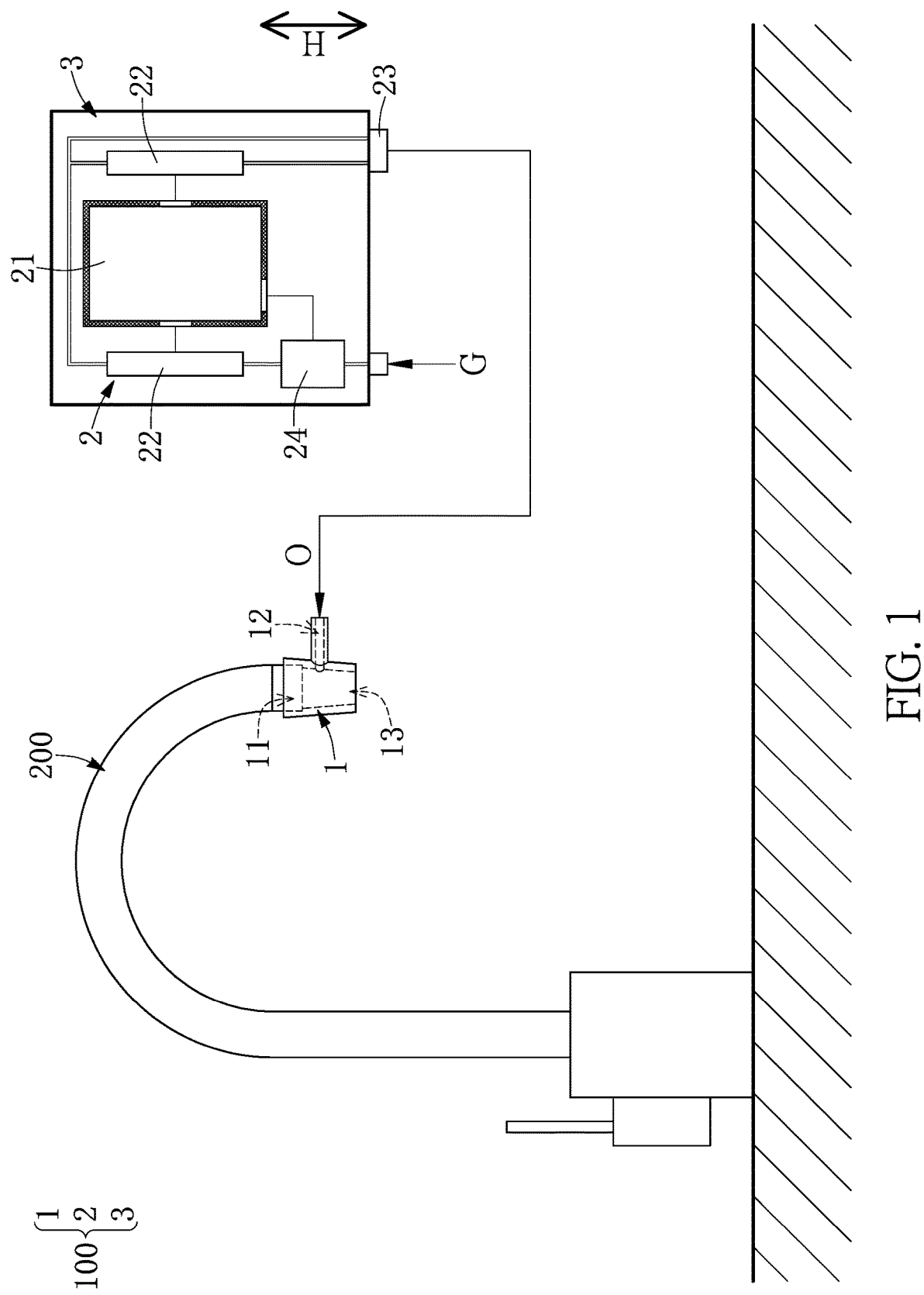
FIG. 1 is a schematic view of an ozone water supply apparatus according to an embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Figure 2:
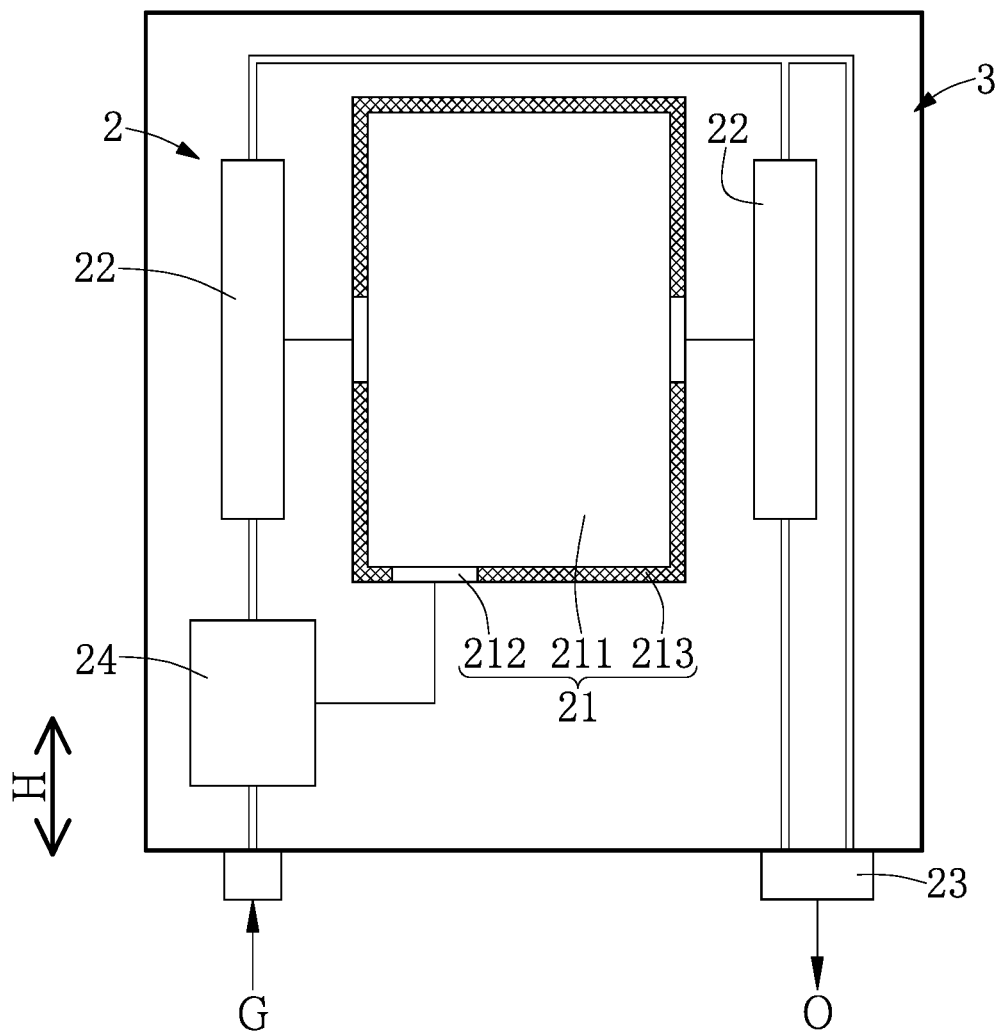
FIG. 2 is a schematic view of an ozone generation device according to the embodiment of the present disclosure.

Referring to FIG. 1 to FIG. 8, an embodiment of the present disclosure provides an ozone water supply apparatus. As shown in FIG. 1 and FIG. 2, the ozone water supply apparatus in the present embodiment includes a faucet device 200 and an ozone generation device 100 assembled to the faucet device 200. The configuration of the faucet device 200 can be adjusted or changed according to design requirements, and the present disclosure is not limited thereto. For example, the faucet device 200 of the present disclosure can be a kitchen faucet or a bathroom faucet.

It should be noted that the ozone generation device 100 in the present embodiment is used in cooperation with the faucet device 200, but the present disclosure is not limited thereto. For example, in other embodiments of the present disclosure, the ozone generation device 100 can be independently applied (e.g., sold) or can be used in cooperation with other devices (e.g., a pipe of a urinal).

The ozone generation device 100 includes a Venturi tube 1, an ozone generation module 2 connected to the Venturi tube 1, and a housing 3 that receives the ozone generation module 2 therein. The Venturi tube 1 is arranged outside of the housing 3. In addition, the ozone generation module 2 in the present embodiment is arranged in the housing 3, but in other embodiments of the present disclosure, the ozone generation device 100 can be provided without the housing 3.

The Venturi tube 1 includes a first entrance 11 (i.e., a liquid entrance), a second entrance 12 (i.e., a gas entrance), and an exit 13 (i.e., a gas-liquid mixed exit). The first entrance 11 of the Venturi tube 1 is connected to the faucet device 200. In other words, when water flows from the faucet device 200 to the Venturi tube 1 through the first entrance 11 and flows out of the Venturi tube 1 through the exit 13, the Venturi tube 1 is configured to form a negative pressure at the second entrance 12. The negative pressure in the present embodiment results in a gas G flowing into the Venturi tube 1 through the second entrance 12.

The ozone generation module 2 includes a circuit unit 21, two ozone-activated tubes 22 electrically coupled to the circuit unit 21, a common pipe 23 connected to the two ozone-activated tubes 22, and a launcher 24 that is electrically coupled to the circuit unit 21. It should be noted that the number of the ozone-activated tubes 22 of the ozone generation module 2 in the present embodiment is two, but the present disclosure is not limited thereto. For example, in other embodiments of the present disclosure, the ozone generation module 2 can include only one ozone-activated tube 22 and not include the common pipe 23, and the ozone-activated tube 22 is detachably assembled in the housing 3 and is in spatial communication with the second entrance 12 of the Venturi tube 1. Accordingly, the number of the ozone-activated tube 22 in the ozone generation module 2 of the present disclosure can be at least one.

In the present embodiment, the circuit unit 21 includes a circuit board 211, a plurality of electrical connectors 212 mounted on the circuit board 211, and a water-proof adhesive 213. The circuit board 211 is substantially embedded in the water-proof adhesive 213, the electrical connectors 212 are exposed from the water-proof adhesive 213, and the circuit board 211 is electrically coupled to the two ozone-activated tubes 22 and the launcher 24 through the electrical connectors 212.

Specifically, most of the circuit board 211 (excluding a portion of the circuit board 211 connected to the electrical connectors 212) is embedded in the water-proof adhesive 213, so that the circuit board 211 in the present embodiment is electrically coupled to other components only through the electrical connectors 212. Accordingly, the circuit board 211 in the present embodiment, which is easily damaged by moisture, is embedded in the water-proof adhesive 213, so that any damage of the circuit board 211 can be effectively avoided, but the present disclosure is not limited thereto.

Moreover, each of the two ozone-activated tubes 22 is detachably assembled in the housing 3 and is in spatial communication with the second entrance 12 of the Venturi tube 1 through the common pipe 23. Furthermore, according to design requirements, the two ozone-activated tubes 22 can be simultaneously driven or alternatively driven by the circuit unit 21.

Specifically, a performance of the ozone-activated tube 22 may decline after being used for a long time, so that the ozone-activated tube 22 in the present embodiment is designed to be detachably assembled in the housing 3 for enabling a user to replace the ozone-activated tube 22 by himself. Moreover, according to design requirements, the two ozone-activated tubes 22 can be spatially communicated with each other in parallel or in series through the common pipe 23, but the present disclosure is not limited thereto.

Figure 3:
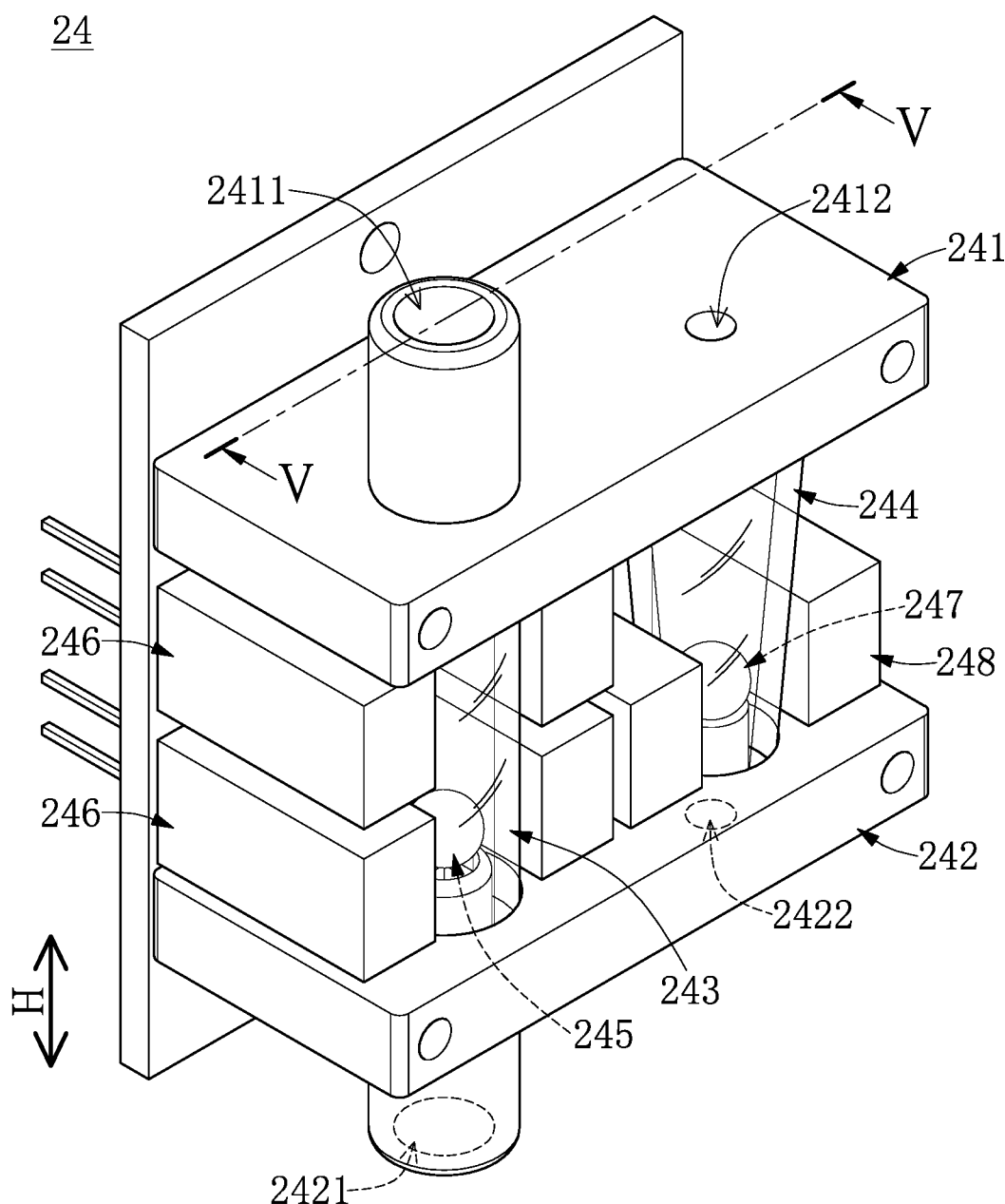
FIG. 3 is a perspective view of a launcher of the ozone generation device according to the embodiment of the present disclosure.
Figure 4:
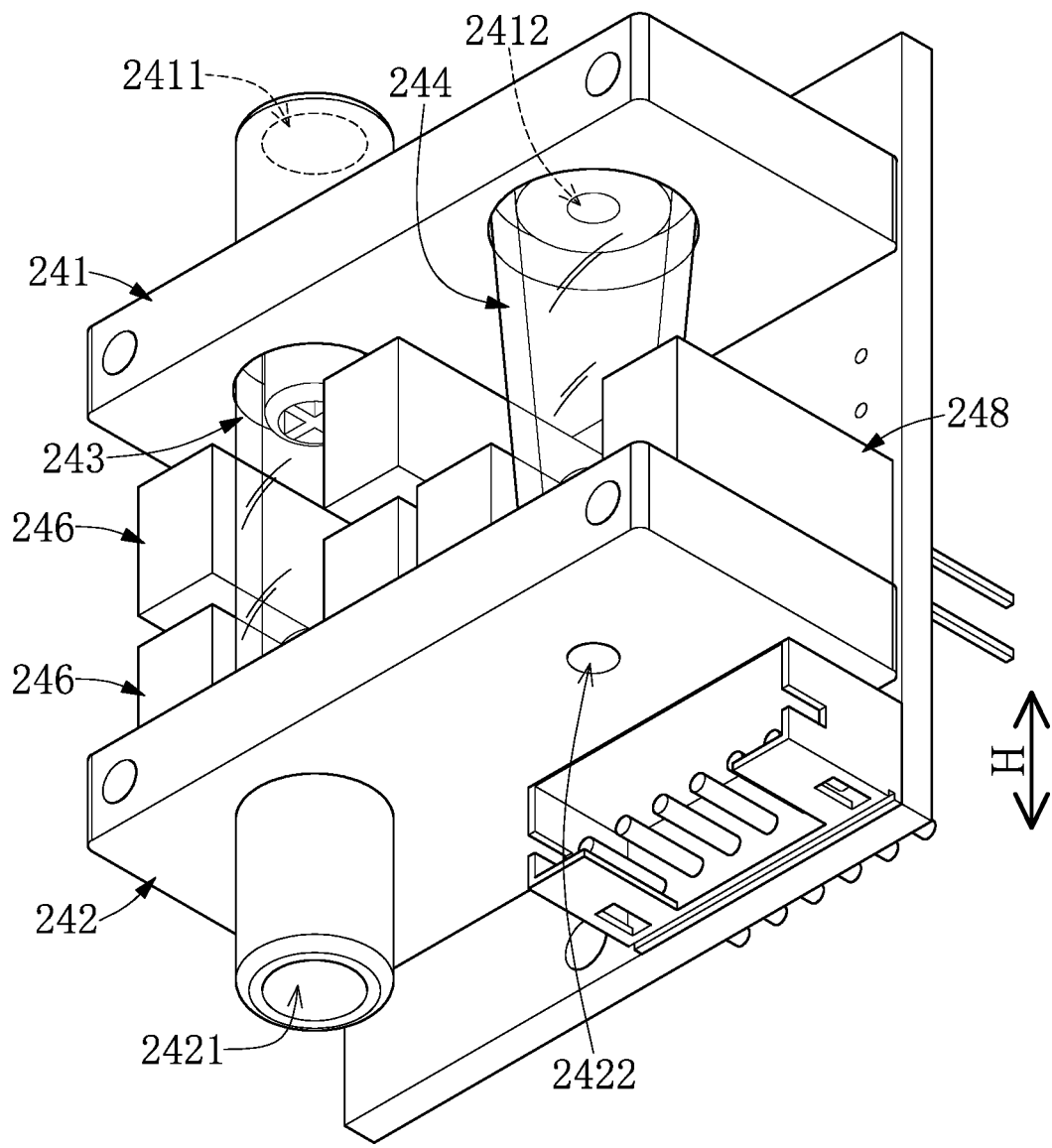
FIG. 4 is a perspective view of the launcher of the ozone generation device from another angle of view according to the embodiment of the present disclosure.
Figure 5:
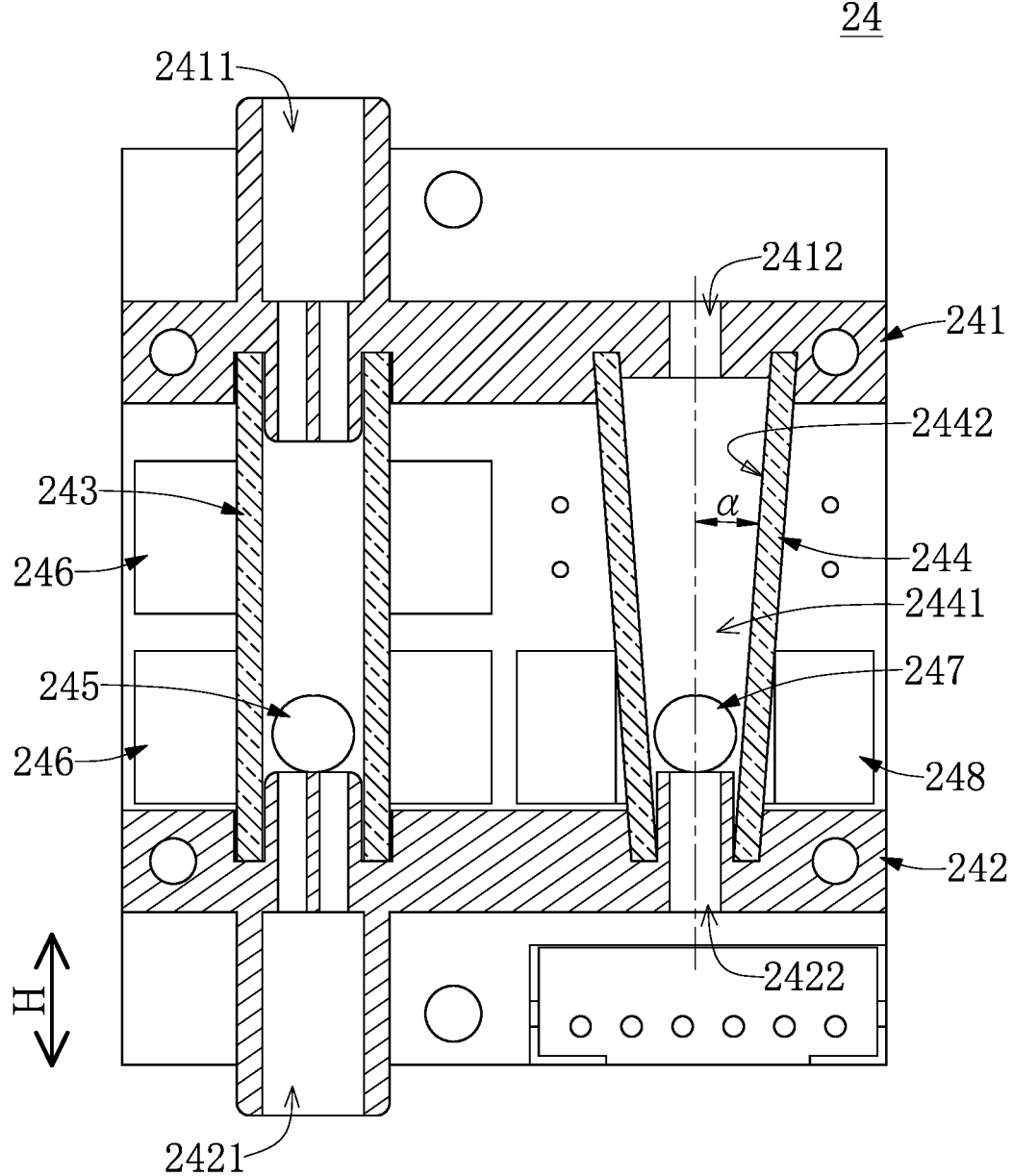
FIG. 5 is a cross-sectional view taken along line V-V of FIG. 3.

As shown in FIG. 3 to FIG. 5, the launcher 24 includes a top retainer 241, a bottom retainer 242 spaced apart from the top retainer 241 along a vertical direction H, a first transparent tube 243 and a second transparent tube 244 both retained between the top retainer 241 and the bottom retainer 242, a floating body 245 arranged in the first transparent tube 243, two first optical detectors 246 arranged outside of the first transparent tube 243, a horizontal member 247 arranged in the second transparent tube 244, and a second optical detector 248 that is arranged outside of the second transparent tube 244.

Each of the top retainer 241 and the bottom retainer 242 is a board structure substantially perpendicular to the vertical direction H. The top retainer 241 has an air-flow exit 2411 that is in spatial communication with at least one of the two ozone-activated tubes 22, and the bottom retainer 242 has an air-flow entrance 2421. The air-flow entrance 2421 and the air-flow exit 2411 in the present embodiment correspond in position to each other along the vertical direction H, but the present disclosure is not limited thereto. Moreover, each of the top retainer 241 and the bottom retainer 242 has a thru-hole 2412, 2422, and the thru-hole 2412 of the top retainer 241 and the thru-hole 2422 of the bottom retainer 242 in the present embodiment also correspond in position to each other along the vertical direction H.

Two opposite ends of the first transparent tube 243 are respectively fixed to the top retainer 241 and the bottom retainer 242, and are respectively in spatial communication with the air-flow exit 2411 and the air-flow entrance 2421. The first transparent tube 243 in the present embodiment is a straight round tube that is parallel to the vertical direction H, but the present disclosure is not limited thereto. For example, in other embodiments of the present disclosure, the first transparent tube 243 can be slantingly arranged with respect to the vertical direction H, and the position of the air-flow entrance 2421 and the position of the air-flow exit 2411 can be adjusted according to the arrangement first transparent tube 243. Or, the first transparent tube 243 can be formed in a prism shape.

The floating body 245 is arranged in the first transparent tube 243, and is located between the air-flow exit 2411 and the air-flow entrance 2421. In the present embodiment, the floating body 245 is an object (e.g., a Styrofoam ball) that is easily blown to move by air. Accordingly, when the gas G flows through the first transparent tube 243 by passing through the air-flow exit 2411 and the air-flow entrance 2421, the gas G can drive the floating body 245 to move along the first transparent tube 243 (e.g., the floating body 245 is moved from the bottom retainer 242 toward the top retainer 241, or the floating body 245 is moved from the air-flow entrance 2421 toward the air-flow exit 2411).

Each of the two first optical detectors 246 are electrically coupled to the circuit unit 21 and are arranged outside of the first transparent tube 243, thereby detecting a movement of the floating body 245. The two first optical detectors 246 in the present embodiment are respectively arranged adjacent to the two ends of the first transparent tube 243, so that the movement of the floating body 245 can be precisely detected by the two first optical detectors 246. It should be noted that though the first optical detector 246 in the present embodiment is an infrared detector, the configuration or structure of the first optical detector 246 can be adjusted or changed according to design requirements, and the present disclosure is not limited thereto.

For example, in other embodiments of the present disclosure, the launcher 24 can include only one first optical detector 246, and the first optical detector 246 is electrically coupled to the circuit unit 21 and is arranged outside of the first transparent tube 243 for detecting the movement of the floating body 245. Accordingly, the number of the first optical detector 246 in the launcher 24 of the present disclosure can be at least one.

Two opposite ends of the second transparent tube 244 are respectively fixed to the top retainer 241 and the bottom retainer 242, and the second transparent tube 244 has a space 2441 therein. The space 2441 of the second transparent tube 244 is in spatial communication with the thru-hole 2412 of the top retainer 241 and the thru-hole 2422 of the bottom retainer 242, but the present disclosure is not limited thereto. For example, in other embodiments of the present disclosure, at least one of the top retainer 241 and the bottom retainer 242 can be formed without the thru-hole 2412, 2422.

Figure 6:
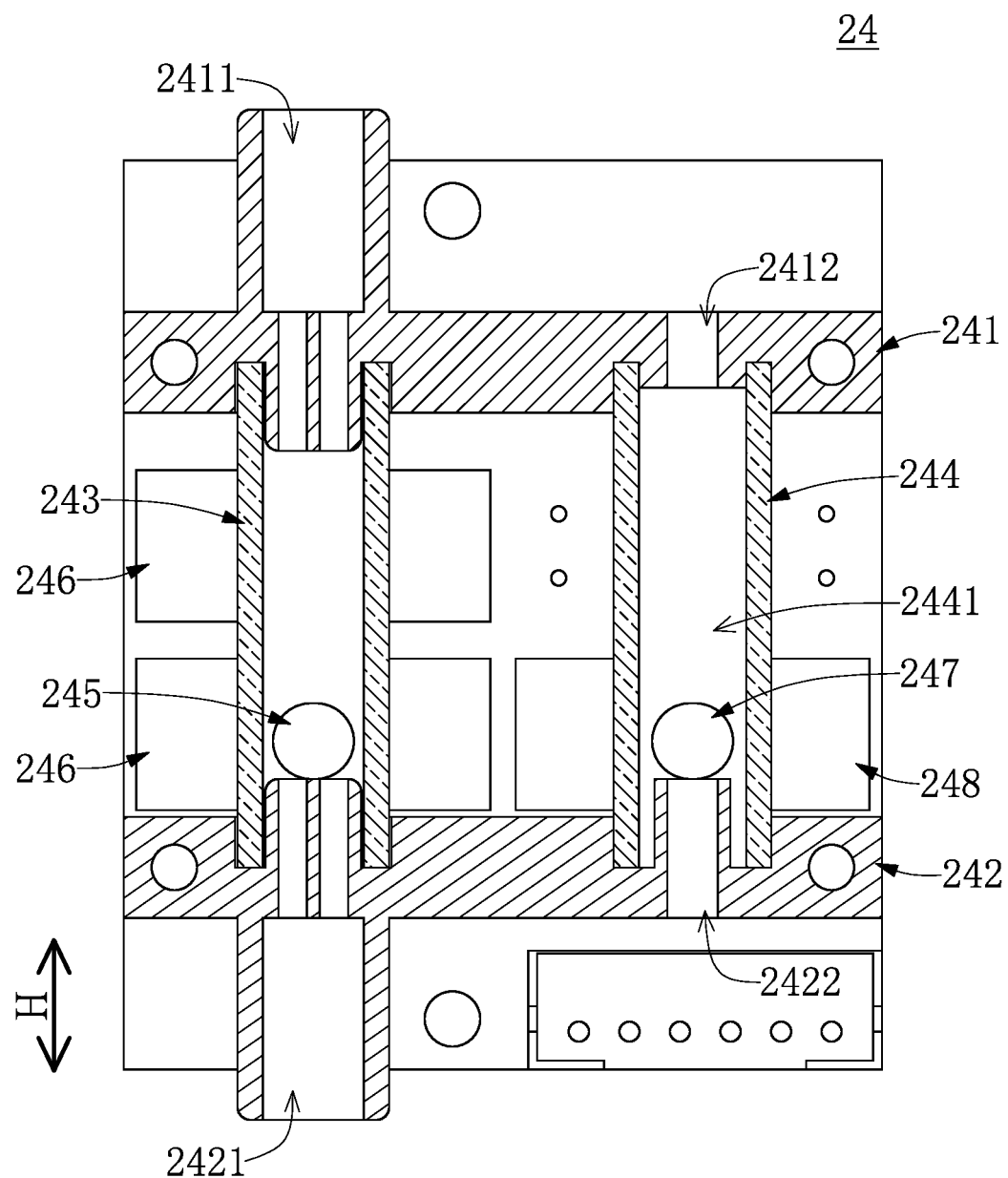
FIG. 6 is a cross-sectional view showing another configuration of FIG. 5.

Specifically, as shown in FIG. 5, in a cross section of the second transparent tube 244 parallel to the vertical direction H, an area surrounded by the second transparent tube 244 (i.e., a volume of the space 2441) is tapered in a direction that extends from the top retainer 241 toward the bottom retainer 242 (e.g., a direction extends from a top end of the second transparent tube 244 to a bottom end of the second transparent tube 244 as shown in FIG. 5), but the present disclosure is not limited thereto. For example, as shown in FIG. 6, the second transparent tube 244 can be a straight round tube that is parallel to the vertical direction H.

As shown in FIG. 5, the second transparent tube 244 in the present embodiment includes a slanting inner wall 2442, and an angle α between the slanting inner wall 2442 and the vertical direction H is within a range of 1-10 degrees. It should be noted that the slanting inner wall 2442 in the cross section of the second transparent tube 244 (as shown in FIG. 5) is preferably a straight line, but the shape of the second transparent tube 244 can be adjusted or changed according to design requirements and is not limited by FIG. 5. For example, in other embodiments of the present disclosure, the slanting inner wall 2442 in the cross section of the second transparent tube 244 can be an arced line.

The horizontal member 247 is arranged in the second transparent tube 244, and is located between the thru-holes 2412, 2422. In the present embodiment, the horizontal member 247 is an object (e.g., a ball) that is easily moved or rolled by gravity. Accordingly, when the ozone generation module 2 is at a slanting position by an external force, the horizontal member 247 is moved along the second transparent tube 244. In other words, the slanting position means a position of the ozone generation module 2 when the gravity drives the horizontal member 247 to move along the second transparent tube 244. In the present embodiment, the structure and connection relationship of each component of the ozone generation module 2 is described when the ozone generation module 2 is not at the slanting position. In other embodiments of the present disclosure, the top retainer 241 and the bottom retainer 242 do not have the thru-holes 2412, 2422, the space 2441 is enclosed by the top retainer 241 and the bottom retainer 242, and the horizontal member 247 is a liquid that is flowable along the second transparent tube 244.

The second optical detector 248 is electrically coupled to the circuit unit 21, and is arranged outside of the second transparent tube 244 for detecting a movement of the horizontal member 247. The second optical detector 248 is arranged adjacent to a portion of the second transparent tube 244 connected to the bottom retainer 242, thereby instantly detecting the movement of the horizontal member 247, but the present disclosure is not limited thereto. It should be noted that the second optical detector 248 in the present embodiment is an infrared detector, but the configuration or structure of the second optical detector 248 can be adjusted or changed according to design requirements.

The above description describes the structure of the ozone water supply apparatus (or the ozone generation device 100), and the following description describes the operation of the ozone water supply apparatus (or the ozone generation device 100) based on the structural design.

Figure 7:
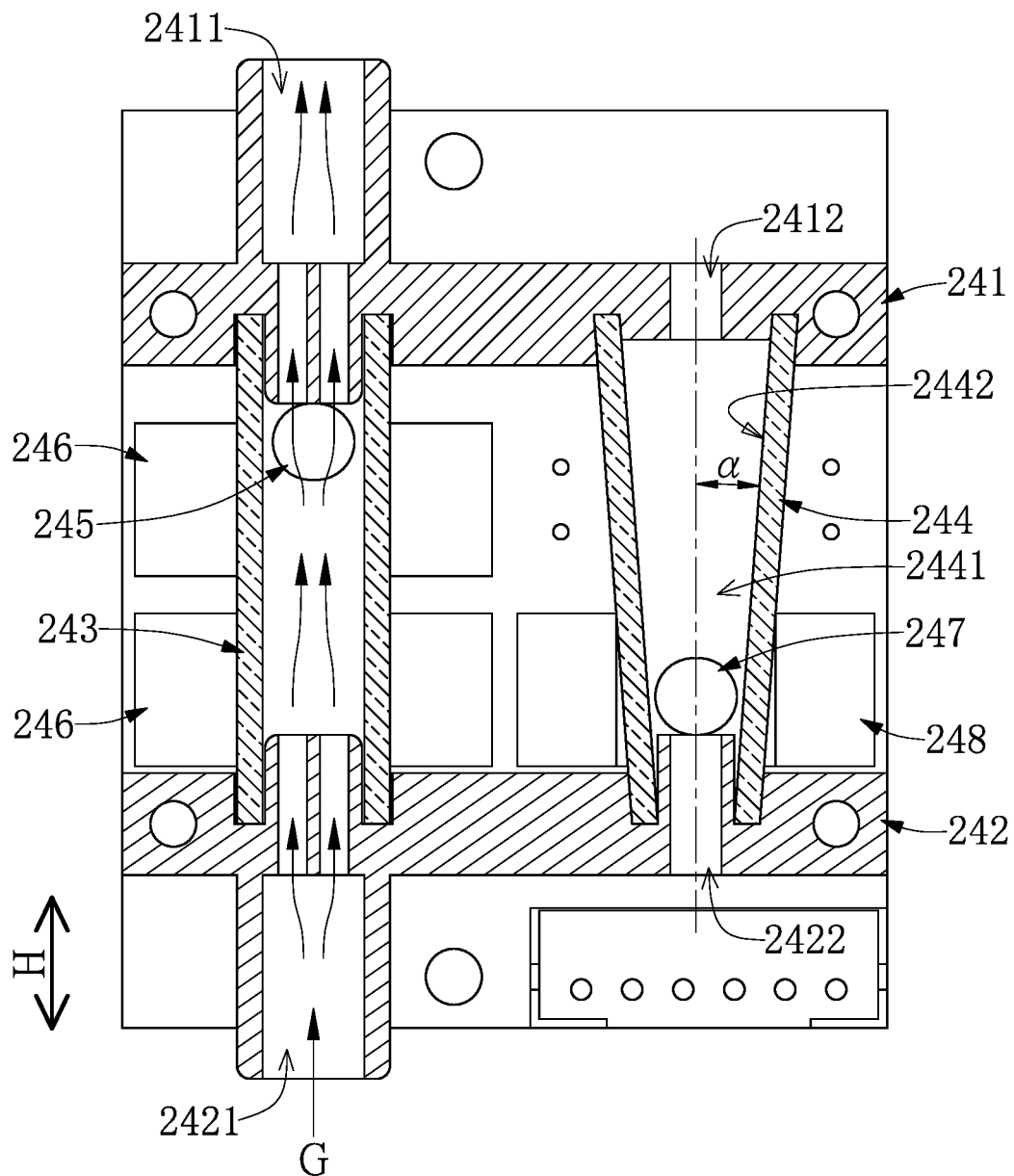
FIG. 7 is a cross-sectional view showing the launcher when the second entrance of the Venturi tube is at the negative pressure.

As shown in FIG. 1, FIG. 2, and FIG. 7, when the Venturi tube 1 forms the negative pressure at the second entrance 12 (i.e., when water flows from the faucet device 200 to the Venturi tube 1 through the first entrance 11 and flows out of the Venturi tube 1 through the exit 13), the gas G flows into the at least one ozone-activated tube 22 by passing through the air-flow entrance 2421, the first transparent tube 243, and the air-flow exit 2411 so as to drive the floating body 245 to move from the bottom retainer 242 toward the top retainer 241. Furthermore, when the movement of the floating body 245 is detected by the at least one first optical detector 246, the at least one first optical detector 246 drives the at least one ozone-activated tube 22 by transmitting a signal to the circuit unit 21 through the corresponding electrical connector 212, so that the at least one ozone-activated tube 22 excites the gas G to become an ozone O that flows toward the second entrance 12.

Accordingly, the ozone water supply apparatus or the ozone generation device 100 of the present disclosure can use the negative pressure generated by the structure of the Venturi tube 1 to drive the gas G to blow against and move the floating body 245, so that the first optical detector 246 can detect the movement of the floating body 245 to instantly obtain a time point when the ozone O needs to be generated. Accordingly, the ozone-activated tube 22 can instantly generate the ozone O toward the Venturi tube 1 (i.e., the ozone-activated tube 22 can sensitively and instantly mix the ozone O into water that flows in the Venturi tube 1).

Figure 8:
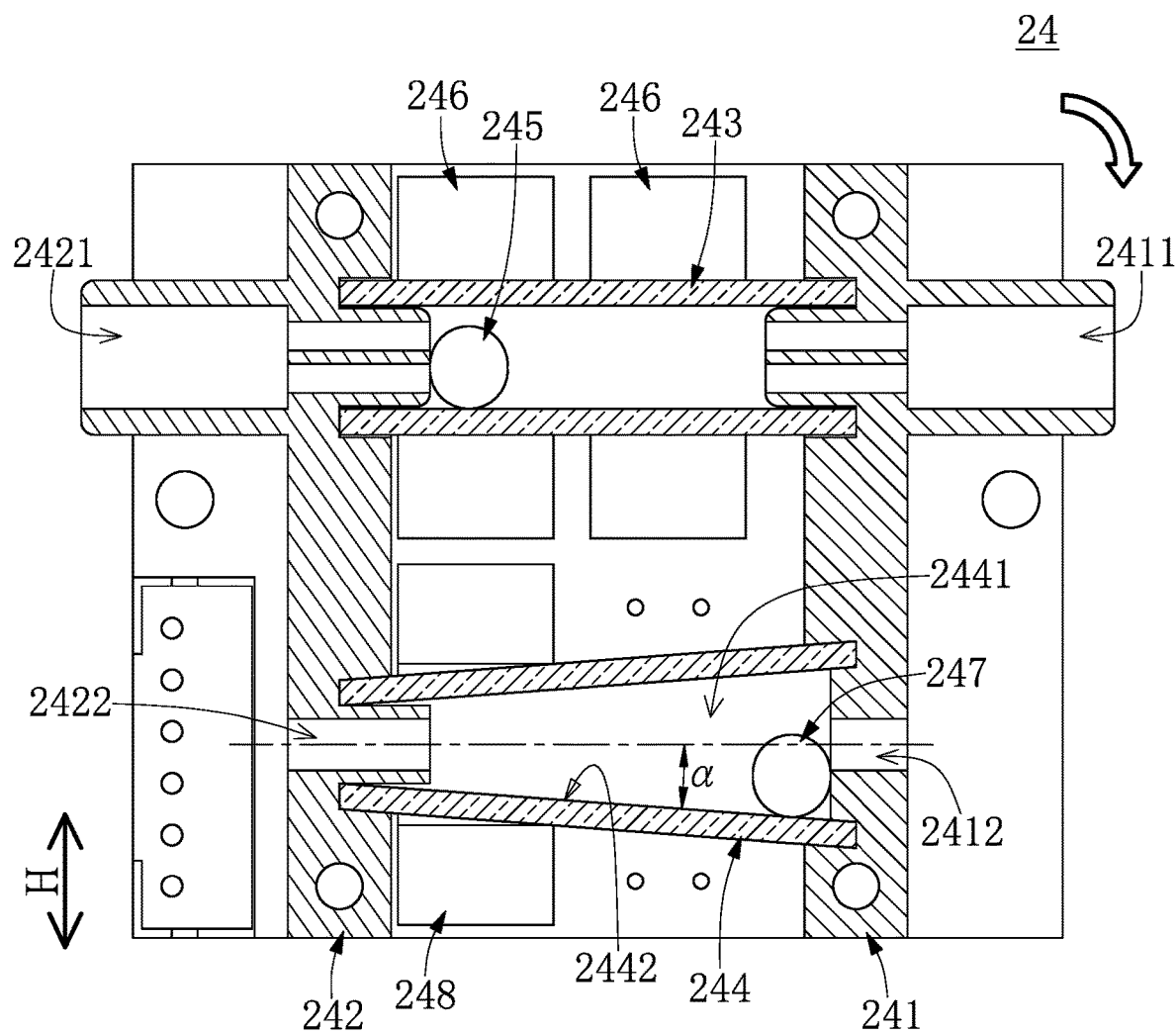
FIG. 8 is a cross-sectional view showing the launcher when the ozone generation device is at a slanting position.

Moreover, as shown in FIG. 2 and FIG. 8, when the second optical detector 248 obtains that the ozone generation module 2 is at the slanting position by detecting the movement of the horizontal member 247, the second optical detector 248 stops the operation of the ozone generation module 2 through the circuit unit 21. Specifically, when the ozone generation module 2 is at the slanting position, the horizontal member 247 is moved out of a detecting area of the second optical detector 248 by the gravity and the slanting inner wall 2442, so that the second optical detector 248 can detect or obtain the movement of the horizontal member 247.

Accordingly, the ozone generation module 2 has an overturning protection mechanism in the launcher 24, thereby effectively preventing the ozone generation module 2 from overturning. In other words, any launcher provided without an overturning protection mechanism is different from the launcher 24 of the present embodiment.

In conclusion, the ozone water supply apparatus or the ozone generation device of the present disclosure can use the negative pressure generated by the structure of the Venturi tube to drive the gas to blow against and move the floating body, so that the first optical detector can detect the movement of the floating body to instantly obtain a time point when an ozone needs to be generated. Accordingly, the ozone-activated tube can instantly generate an ozone toward the Venturi tube.

Moreover, a performance of the ozone-activated tube may decline caused by a dust collection after being used for a long time, so that ozone generation device in the present disclosure has more than one ozone-activated tube, and any one of the ozone-activated tubes is designed to be detachably assembled in the housing for enabling a user to replace it by himself. Furthermore, according to design requirements, the two ozone-activated tubes can be simultaneously driven or alternatively driven by the circuit unit.

In addition, most of the circuit board (excluding a portion of the circuit board connected to the electrical connectors) is embedded in the water-proof adhesive, so that the circuit board in the present disclosure is electrically coupled to other components only through the electrical connectors. Accordingly, the circuit board in the present disclosure, which is easily damaged by moisture, is embedded in the water-proof adhesive, so that any damage of the circuit board can be effectively avoided.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. An ozone water supply apparatus, comprising:
a faucet device; and
an ozone generation device including:
a Venturi tube including a first entrance connected to the faucet device, a second entrance, and an exit, wherein when water flows from the faucet device to the Venturi tube through the first entrance and flows out of the Venturi tube through the exit, the Venturi tube is configured to form a negative pressure at the second entrance; and
an ozone generation module including:
a circuit unit;
at least one ozone-activated tube electrically coupled to the circuit unit and being in spatial communication with the Venturi tube through the second entrance; and
a launcher electrically coupled to the circuit unit and including:
a top retainer and a bottom retainer that is spaced apart from the top retainer along a vertical direction, wherein the top retainer has an air-flow exit in spatial communication with the at least one ozone-activated tube, and the bottom retainer has an air-flow entrance;
a first transparent tube having two opposite ends respectively fixed to the top retainer and the bottom retainer and being respectively in spatial communication with the air-flow exit and the air-flow entrance;
a floating body arranged in the first transparent tube, wherein when a gas flows through the first transparent tube by passing through the air-flow entrance and the air-flow exit, the gas drives the floating body to move from the bottom retainer toward the top retainer;
at least one first optical detector electrically coupled to the circuit unit and arranged outside of the first transparent tube for detecting a movement of the floating body;
a second transparent tube having two ends respectively fixed to the top retainer and the bottom retainer, wherein the second transparent tube has a space therein;
a horizontal member arranged in the second transparent tube, wherein when the ozone generation module is at a slanting position by an external force, the horizontal member is moved along the second transparent tube; and
a second optical detector electrically coupled to the circuit unit and arranged outside of the second transparent tube for detecting a movement of the horizontal member, wherein when the second optical detector obtains that the ozone generation module is at the slanting position by detecting the movement of the horizontal member, the second optical detector stops the operation of the ozone generation module through the circuit unit;
wherein when the Venturi tube forms the negative pressure at the second entrance, the gas flows into the at least one ozone-activated tube by passing through the air-flow entrance, the first transparent tube, and the air-flow exit so as to drive the floating body to move from the bottom retainer toward the top retainer, and wherein when the movement of the floating body is detected by the at least one first optical detector, the at least one first optical detector drives the at least one ozone-activated tube through the circuit unit, so that at least one ozone-activated tube excites the gas to become an ozone that flows toward the second entrance.

2. The ozone water supply apparatus according to claim 1, wherein in a cross section of the second transparent tube parallel to the vertical direction, an area surrounded by the second transparent tube is tapered along a direction extending from the top retainer toward the bottom retainer.

3. The ozone water supply apparatus according to claim 2, wherein the second transparent tube includes a slanting inner wall, and an angle between the slanting inner wall and the vertical direction is within a range of 1-10 degrees.

4. The ozone water supply apparatus according to claim 1, wherein the number of the at least one ozone-activated tube is two, the ozone generation module includes a common pipe connected to the two ozone-activated tubes, and the two ozone-activated tubes are configured to be simultaneously driven or alternatively driven.

5. The ozone water supply apparatus according to claim 1, wherein the ozone generation device includes a housing receiving the ozone generation module, the Venturi tube is arranged outside of the housing, and the at least one ozone-activated tube is detachably assembled to the housing.

6. The ozone water supply apparatus according to claim 5, wherein the circuit unit includes a circuit board, a plurality of electrical connectors mounted on the circuit board, and a water-proof adhesive, and wherein the circuit board is embedded in the water-proof adhesive, the electrical connectors are exposed from the water-proof adhesive, and the circuit board is electrically coupled to the at least one ozone-activated tube and the launcher through the electrical connectors.

7. The ozone water supply apparatus according to claim 1, wherein the number of the at least one first optical detector is two, and the two first optical detectors are respectively arranged adjacent to the two ends of the first transparent tube.

8. An ozone generation device, comprising:
a Venturi tube including a first entrance, a second entrance, and an exit, wherein the Venturi tube is configured to provide water to flow there-into through the first entrance and to flow there-out through the exit so as to form a negative pressure at the second entrance; and
an ozone generation module including:
a circuit unit;
at least one ozone-activated tube electrically coupled to the circuit unit and being in spatial communication with the Venturi tube through the second entrance; and
a launcher electrically coupled to the circuit unit and including:
a top retainer and a bottom retainer that is spaced apart from the top retainer along a vertical direction, wherein the top retainer has an air-flow exit in spatial communication with the at least one ozone-activated tube, and the bottom retainer has an air-flow entrance;
a first transparent tube having two opposite ends respectively fixed to the top retainer and the bottom retainer and being respectively in spatial communication with the air-flow exit and the air-flow entrance;
a floating body arranged in the first transparent tube, wherein when a gas flows through the first transparent tube by passing through the air-flow entrance and the air-flow exit, the gas drives the floating body to move from the bottom retainer toward the top retainer;

at least one first optical detector electrically coupled to the circuit unit and arranged outside of the first transparent tube for detecting a movement of the floating body;

a second transparent tube having two ends respectively fixed to the top retainer and the bottom retainer, wherein the second transparent tube has a space therein;

a horizontal member arranged in the second transparent tube, wherein when the ozone generation module is at a slanting position by an external force, the horizontal member is moved along the second transparent tube; and a second optical detector electrically coupled to the circuit unit and arranged outside of the second transparent tube for detecting a movement of the horizontal member, wherein when the second optical detector obtains that the ozone generation module is at the slanting position by detecting the movement of the horizontal member, the second optical detector stops the operation of the ozone generation module through the circuit unit;

wherein when the Venturi tube forms the negative pressure at the second entrance, the gas flows into the at least one ozone-activated tube by passing through the air-flow entrance, the first transparent tube, and the air-flow exit so as to drive the floating body to move from the bottom retainer toward the top retainer, and wherein when the movement of the floating body is detected by the at least one first optical detector, the at least one first optical detector drives the at least one ozone-activated tube through the circuit unit, so that at least one ozone-activated tube excites the gas to become an ozone that flows toward the second entrance.

9. The ozone generation device according to claim 8, wherein in a cross section of the second transparent tube parallel to the vertical direction, an area surrounded by the second transparent tube is tapered along a direction extending from the top retainer toward the bottom retainer.

10. The ozone generation device according to claim 9, wherein the second transparent tube includes a slanting inner wall, and an angle between the slanting inner wall and the vertical direction is within a range of 1-10 degrees.

* * * * *